United States Patent
Behabtu et al.

(10) Patent No.: US 10,995,435 B2
(45) Date of Patent: *May 4, 2021

(54) NONWOVEN GLUCAN WEBS

(71) Applicant: NUTRITION & BIOSCIENCES USA 4, INC., Rochester, NY (US)

(72) Inventors: Natnael Behabtu, Wilmington, DE (US); Joseph F. Roeske, Salem, NJ (US); Yefim Brun, Wilmington, DE (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 223 days.

This patent is subject to a terminal disclaimer.

(21) Appl. No.: 15/763,965

(22) PCT Filed: Nov. 8, 2016

(86) PCT No.: PCT/US2016/060892
§ 371 (c)(1),
(2) Date: Mar. 28, 2018

(87) PCT Pub. No.: WO2017/083244
PCT Pub. Date: May 18, 2017

(65) Prior Publication Data
US 2018/0282918 A1    Oct. 4, 2018

Related U.S. Application Data

(60) Provisional application No. 62/253,319, filed on Nov. 10, 2015.

(51) Int. Cl.
| | |
|---|---|
| C08B 37/00 | (2006.01) |
| D01F 9/00 | (2006.01) |
| D01D 5/14 | (2006.01) |
| C08L 5/00 | (2006.01) |
| D04H 1/724 | (2012.01) |
| D04H 3/08 | (2006.01) |
| D04H 1/4326 | (2012.01) |
| D04H 3/009 | (2012.01) |
| C12P 19/18 | (2006.01) |
| D04H 1/4258 | (2012.01) |
| D04H 3/013 | (2012.01) |

(52) U.S. Cl.
CPC ....... *D04H 1/4326* (2013.01); *C08B 37/0009* (2013.01); *C08L 5/00* (2013.01); *C12P 19/18* (2013.01); *D01D 5/14* (2013.01); *D01F 9/00* (2013.01); *D04H 1/4258* (2013.01); *D04H 1/724* (2013.01); *D04H 3/009* (2013.01); *D04H 3/013* (2013.01); *D04H 3/08* (2013.01); *D10B 2331/30* (2013.01)

(58) Field of Classification Search
None
See application file for complete search history.

(56) References Cited

U.S. PATENT DOCUMENTS

| | | |
|---|---|---|
| 5,041,252 A | 8/1991 | Fujii et al. |
| 7,000,000 B1 | 2/2006 | O'Brien |
| 8,871,474 B2 | 10/2014 | Payne et al. |
| 2013/0161562 A1* | 6/2013 | O'Brien ............... C08K 3/22 252/363.5 |
| 2016/0138195 A1 | 5/2016 | Kraft et al. |
| 2016/0177471 A1* | 6/2016 | Kraft ................... D04H 1/4258 442/304 |

FOREIGN PATENT DOCUMENTS

| | | | |
|---|---|---|---|
| WO | 2014201481 A1 | 12/2014 | |
| WO | 2014201482 A1 | 12/2014 | |
| WO | WO-2014201481 A1 * | 12/2014 | ............. B29C 48/02 |

OTHER PUBLICATIONS

International Preliminary Report on Patentability—PCT/US2016/060892—dated May 24, 2018.

* cited by examiner

*Primary Examiner* — Layla D Berry

(57) ABSTRACT

Nonwoven webs comprising a water insoluble α-(1,3→glucan) polymer and methods of forming the nonwoven webs are disclosed. The water insoluble α-(1,3→glucan) polymer comprises 90% or greater α-1,3-glycosidic linkages, less than 1% by weight of α-1,3,6-glycosidic branch points, a number average degree of polymerization in the range of from 55 to 10,000, and a ratio of apparent DPw to true DPw in the range of from 2 to 10. The nonwoven webs can be used for personal hygiene wipes, filtration media, apparel, or other uses.

27 Claims, No Drawings

NONWOVEN GLUCAN WEBS

CROSS-REFERENCE TO RELATED APPLICATION

This application is the National Stage application of International Application No. PCT/US2016/060892 (filed Nov. 8, 2016), which claims the benefit of priority of U.S. Provisional Application No. 62/253,319 filed Nov. 10, 2015, all of which prior applications are incorporated by reference herein in their entirety.

FIELD OF THE DISCLOSURE

The present disclosure is directed towards a nonwoven web of a water insoluble α-(1,3→glucan) polymer and processes for producing the web.

BACKGROUND

Nonwoven webs are important materials in industry today. Many of the medical care garments, protective wear garments, mortuary and veterinary products and personal care products in use today are partially or wholly constructed of nonwoven web materials. Examples of such products include everyday items like personal hygiene wipes, diapers, training pants, swimwear, incontinence garments, pads, sanitary napkins, as well as antimicrobial surgical gowns and bandages, protective workwear garments such as coveralls and lab coats and the like. Nonwoven fibrous webs provide tactile, comfort, and aesthetic properties that can approach those of traditional woven or knitted cloth materials. Nonwoven web materials are also widely used as filtration medial for both liquid and gas or air filtration applications (e.g., high efficiency particle air (HEPA) filtration) since they can be formed into a filter mesh of fine fibers having a low average pore size suitable for trapping particulate matter while still having a low pressure drop across the mesh.

Nonwoven web materials have a physical structure of individual fibers or filaments that are interlaid in a generally random manner rather than in a regular, identifiable manner as in a knitted or woven fabric. The fibers of a nonwoven web may be continuous or discontinuous, and, are frequently made from thermoplastic polymer or copolymer resins from the general classes of polyolefins, polyesters, and polyamides, as well as numerous other polymers.

Various methods have been disclosed for preparing nonwoven webs. In general, the first step is to produce the web of fibers, for example by dry-laid, wet-laid, or molten polymer laid methods. Once the initial webs have been formed, they can be consolidated to increase the structural integrity by bonding at least a portion of the fibers together. Bonding can occur via chemical, mechanical, thermal, solvent bonding, or other methods. Finally, webs can have an optional finishing step which applies one or more treatments to improve the properties of the nonwoven web. Some examples of properties that can be improved by the finishing treatments can include dye uptake, absorbency, repellency, texture, and antimicrobial activity.

The majority of the nonwoven webs on the market today are produced from man-made polymers. There is a continuing need for producing nonwoven webs from polymers made from renewable resources.

SUMMARY

The disclosure relates to a process of forming a nonwoven web, wherein the process comprises:

a) introducing an aqueous solution of a water insoluble α-(1,3→glucan) polymer into a chamber;
b) contacting a pressurized gas with the aqueous solution of step (a) in the chamber to form fibers; and
c) collecting the fibers to form a nonwoven web;

wherein the aqueous solution comprises the water insoluble α-(1,3→glucan) polymer in an aqueous base, and wherein the water insoluble α-(1,3→glucan) polymer has a ratio of apparent DPw to true DPw in the range of from 2 to 15.

The disclosure also relates to a nonwoven web comprising a water insoluble α-(1,3→glucan) polymer, wherein the water insoluble α-(1,3→glucan) polymer comprises 90% or greater α-1,3-glycosidic linkages, less than 1% by weight of α-1,3,6-glycosidic branch points, a number average degree of polymerization in the range of from 55 to 10,000, and a ratio of apparent DPw to true DPw in the range of from 2 to 10.

DETAILED DESCRIPTION

The disclosures of all cited patent and non-patent literature are incorporated herein by reference in their entirety.

As used herein, the term "embodiment" or "disclosure" is not meant to be limiting, but applies generally to any of the embodiments defined in the claims or described herein. These terms are used interchangeably herein.

Unless otherwise disclosed, the terms "a" and "an" as used herein are intended to encompass one or more (i.e., at least one) of a referenced feature.

The features and advantages of the present disclosure will be more readily understood, by those of ordinary skill in the art from reading the following detailed description. It is to be appreciated that certain features of the disclosure, which are, for clarity, described above and below in the context of separate embodiments, may also be provided in combination in a single element. Conversely, various features of the disclosure that are, for brevity, described in the context of a single embodiment, may also be provided separately or in any sub-combination. In addition, references to the singular may also include the plural (for example, "a" and "an" may refer to one or more) unless the context specifically states otherwise.

The use of numerical values in the various ranges specified in this application, unless expressly indicated otherwise, are stated as approximations as though the minimum and maximum values within the stated ranges were both proceeded by the word "about". In this manner, slight variations above and below the stated ranges can be used to achieve substantially the same results as values within the ranges. Also, the disclosure of these ranges is intended as a continuous range including each and every value between the minimum and maximum values.

As used herein:

The phrase "water insoluble" means that less than 5 grams of the substance, for example, the α-(1,3→glucan) polymer dissolves in 100 milliliters of water at 23° C. In other embodiments, water insoluble means that less than 4 grams or 3 grams or 2 grams or 1 gram of the substance dissolves in water at 23° C.

The phrase "α-(1,3→glucan) polymer" means a polysaccharide comprising glucose monomer units linked together by glycosidic linkages wherein at least 50% of the glycosidic linkages are α-1,3-glycosidic linkages. In other embodiments, the percentage of α-1,3-glycosidic linkages can be greater than or equal to 90%, 95%, 96%, 97%, 98%, 99% or 100% (or any integer value between 50% and 100%). Accordingly, the α-(1,3→glucan) polymer comprises less than or equal to 10%, 5%, 4%, 3%, 2%, 1% or 0% of glycosidic linkages that are not α-1,3-glycosidic linkages. The α-(1,3→glucan) polymer also has a number average degree of polymerization in the range of from 55 to 10,000.

The terms "glycosidic linkage" refers to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. Herein, "alpha-D-glucose" will be referred to as "glucose".

The phrase "aqueous solution" refers to a solution of the water insoluble α-(1,3→glucan) polymer in an aqueous base. In some embodiments, the aqueous solution comprises or consists essentially of the water insoluble α-(1,3→glucan) polymer, water, and sodium hydroxide, and/or potassium hydroxide. The aqueous base can be aqueous sodium hydroxide, aqueous potassium hydroxide, aqueous lithium hydroxide, or a combination thereof. In other embodiments, the aqueous base comprises aqueous sodium hydroxide or aqueous potassium hydroxide. In another embodiment, the aqueous base can be aqueous sodium hydroxide. In yet another embodiment, the aqueous base can be aqueous potassium hydroxide. In some embodiments, the aqueous solution can further comprise one or more non-aqueous solvents, for example less than or equal to 20% by weight, based on the total weight of the water of the non-aqueous solvent. In other embodiments, the non-aqueous solvent comprises less than or equal to 10% or 5% or 4% or 3% or 2% or 1% by weight, based on the total amount of the water and the non-aqueous solvent. Non-aqueous solvents can include, for example, methanol, ethanol, dimethyl sulfoxide, dimethyl acetamide, dimethyl formamide, ethylene glycol, or a combination thereof.

The term "isotropic solution" refers to a solution exhibiting a disordered morphology. Isotropic solutions stand in contrast with the morphology of liquid crystalline solutions that exhibit ordered regions as described in U.S. Pat. No. 7,000,000. It has surprisingly been found that the aqueous solution of the water insoluble α-(1,3→glucan) polymer is isotropic and useful for the preparation of nonwoven webs.

The phrase "consists essentially of" or "consisting essentially of" means that a composition contains all of the recited components and less than 5% by weight, based on the total weight of the composition of any other component or combination of components. For example, a composition consisting essentially of A and B must contain at least 95% by weight of A and B and no more than 5% by weight of any other component or combination components, wherein the percentage by weight is based on the total weight of the composition. In other embodiments, the phrase consisting essentially of means that the composition contains less than 4% or 3% or 2% or 1% or less than 0.5% by weight of the components that are not recited, based on the total weight of the composition.

The "molecular weight" of the water insoluble α-(1,3→glucan) polymer herein can be represented as number-average molecular weight (Mn) or as weight-average molecular weight (Mw), the units of which are in Daltons or grams/mole. Alternatively, molecular weight can be represented as DPw (weight average degree of polymerization) or DPn (number average degree of polymerization). The molecular weights and degrees of polymerization are related. For example, DPw can be calculated from the Mw by dividing the Mw by 162.14. Various means are known in the art for performing these molecular weight measurements, such as with high-pressure liquid chromatography (HPLC) or size exclusion chromatography (SEC).

The term "fibers" refers to both staple length fibers and continuous fibers.

As used herein the term "nonwoven web" means a web having a structure of individual fibers or filaments which are interlaid, but not in an identifiable manner as in a knitted or woven fabric.

The "apparent DPw" and "true DPw" are determined via the following method: a sample of the water insoluble α-(1,3→glucan) polymer was added to a mixture of dimethyl acetamide (DMAc, available from J.T. Baker, Phillipsburg, N.J.) with 5% lithium chloride (LiCl, available from Sigma-Aldrich, St. Louis, Mo.). The sample was stirred for two hours at a temperature of 100-105° C. After two hours of stirring, the sample was removed and the weight average degree of polymerization (DPw) was determined by size exclusion chromatography (SEC) with an Alliance 2695™ chromatograph (available from Waters Corporation, Milford, Mass.) equipped with two ZORBAX® PSM Bimodal-s silica columns (Agilent, Wilmington, Del.), a refractive index detector 2414 from Waters Corporation and a HELEOS II™ multiangle light scattering photometer (available from Wyatt Technologies, Santa Barbara, Calif.) using DMAc with 0.1% LiCl as the mobile phase. This DPw was labeled as the "apparent DPw". The stirring of the water insoluble α-(1,3→glucan) polymer in a mixture of DMAc with 5% LiCl was continued at 100-105° C. for at least 18 hours. After 18 hours of stirring, another sample was removed and the DPw was determined using the same method. This DPw was labeled as the "true DPw". In some embodiments, the ratio of the apparent DPw to the true DPw is in the range of from 2 to 15.

The nonwoven web comprises or consists essentially of the water insoluble α-(1,3→glucan) polymer having 90% or greater α-1,3-glycosidic linkages, less than 1% weight of α-1,3,6-glycosidic branch points, and a number average degree of polymerization in the range of from 55 to 10,000. In an additional embodiment, the nonwoven web further comprises a ratio of apparent DPw to true DPw in the range of from 2 to 10. In other embodiments, the nonwoven web comprises or consists essentially of the water insoluble α-(1,3→glucan) polymer having 95% or greater α-1,3-glycosidic linkages, less than 1% by weight of α-1,3,6-glycosidic branch points, and a number average degree of polymerization in the range of from 55 to 10,000. In still further embodiments, the nonwoven web comprises or consists essentially of the water insoluble α-(1,3→glucan) polymer having 99% or greater α-1,3-glycosidic linkages, less that 1% by weight of α-1,3,6-glycosidic branch points and a number average degree of polymerization in the range of from 55 to 10,000.

The disclosure also relates to a process of forming the nonwoven web, wherein the process comprises:

a) introducing an aqueous solution of a water insoluble α-(1,3→glucan) polymer into a chamber;

b) contacting a pressurized gas with the aqueous solution of step (a) in the chamber to form fibers; and c) collecting the fibers to form a nonwoven web;

wherein the aqueous solution comprises the water insoluble α-(1,3→glucan) polymer in an aqueous base, and wherein the water insoluble α-(1,3→glucan) polymer has a ratio of apparent DPw to true DPw in the range of from 2 to 15.

The water insoluble α-(1,3→glucan) polymer can be produced using an enzymatic method, for example, a method using glucosyl transferase enzymes as provided by U.S. Pat. No. 7,000,000 or U.S. Pat. No. 8,871,474. In some embodiments, the water insoluble α-(1,3→glucan) polymer is produced by a glucosyltransferase enzyme having 90% or greater sequence identity to Gtf J. An enzymatic production of the water insoluble α-(1,3→glucan) polymer can result in a number average degree of polymerization (DPn) in the range of from 55 to 10,000. In other embodiments, the DPn can be in the range of from 75 to 1,000 and, in still further embodiments, in the range of from 100 to 800. The number average degree of polymerization can be determined by size exclusion chromatography. The DPn can be determined using the same process as is given above for determining the true DPw. The ratio of the apparent DPw to true DPw is in the range of from 2 to 15, in other words, the ratio is greater than or equal to 2 and less than or equal to 15. In other embodiments, the ratio of the apparent DPw to the true DPw is in the range of from 2 to 14 or from 2 to 13 or from 2 to 12 or from 2 to 11 or from 2 to 10.

The enzymes disclosed in the above references are also particularly useful for producing water insoluble α-(1,3→glucan) polymer having greater than or equal to 90% α-1,3-glycosidic linkages. The water insoluble α-(1,3→glucan) polymer comprising greater than or equal to 90% α-1,3-glycosidic linkages is herein to be considered a linear polymer having a homogeneous structure. By homogeneous structure is meant that the water insoluble α-(1,3→glucan) polymer has less than 10% linkages that are not α-1,3-glycosidic linkages, for example, α-1,6-glycosidic linkages, α-1,4-glycosidic linkages or α-1,3,6-glycosidic branch points. In other embodiments, the water insoluble α-(1,3→glucan) polymer comprises greater than or equal to 91% α-1,3-glycosidic linkages or greater than or equal to 92% or 93% or 94% or 95% or 96% or 97% or 98% or 99% α-1,3-glycosidic linkages and less than 9% or 8% or 7% or 6% or 5% or 4% or 3% or 2% or 1% of glycosidic linkages that are not α-1,3-linkages. In still further embodiments, the water insoluble α-(1,3→glucan) polymer is a linear polymer having greater than or equal to 99% of α-1,3-glycosidic linkages and less than 1% α-1,3,6-glycosidic branch points.

As used herein the percentage of α-1,3-glycosidic linkages refers to the average number of monomer units that are linked via α-1,3-glycosidic linkages divided by the total number of monomer units in the polymer composition (×100). The percentage of α-1,3-glycosidic linkages is determined via integration of the peaks in a $^1$H NMR spectra, wherein a sample of the water insoluble α-(1,3→glucan) polymer is dissolved in $d_6$-dimethyl sulfoxide (DMSO) containing 3 percent by weight LiCl and 0.1 milliliters of trifluoroacetic acid in $d_6$-DMSO. The percentages of linkages that are not α-1,3-glycosidic linkages can be determined in the same manner and using the same general formula.

In order to form the aqueous solution of the water insoluble α-(1,3→glucan) polymer, the polymer is dispersed and/or dissolved in an aqueous base, for example, aqueous alkali metal hydroxide, aqueous sodium hydroxide, aqueous potassium hydroxide, or aqueous lithium hydroxide. In some embodiments, the alkali metal hydroxide is sodium hydroxide, while in other embodiments, the alkali metal hydroxide is potassium hydroxide. Combinations of both sodium hydroxide and potassium hydroxide can also be used. The concentration of the alkali metal hydroxide in the aqueous base can be in the range of from 2 to 10% by weight, based on the total weight of the water and the alkali metal hydroxide. In other embodiments, the concentration of the alkali metal hydroxide can be in the range of from 3 to 9% by weight or from 4 to 8% by weight, wherein the percentages by weight are based on the total weight of water and the alkali metal hydroxide.

The water insoluble α-(1,3→glucan) polymer can be present in the aqueous solution in the range of from 5% to 20% by weight, based on the total weight of the aqueous solution. In other embodiments, the water insoluble α-(1,3→glucan) polymer can be present in the range of from 7 to 19% by weight or from 9 to 18% by weight or from 10 to 17% by weight or from 11 to 16% by weight, wherein the percentages by weight are based on the total weight of the aqueous solution. The aqueous solution can be prepared by adding the water insoluble α-(1,3→glucan) polymer to the aqueous base and agitating until a solution forms. The water insoluble α-(1,3→glucan) polymer can be added to the aqueous alkali metal hydroxide all at once, portionwise, or as a slurry in water.

The aqueous solution can further comprise one or more additives, for example, pigments, dyes, rheology modifiers, toughening agents, fillers, antimicrobial agents, flame retardants, light stabilizers, UV absorbers or a combination thereof. The additives can be present in the range of from 0% to 50% by weight, based on the weight of the water insoluble α-(1,3→glucan) polymer present in the aqueous solution. In other embodiments, the additives can be present in the range of from 0% to 49% or 0% to 30% or 0 to 20% or 0% to 10% by weight, based on the total weight of the water insoluble α-(1,3→glucan) polymer in the aqueous solution. Additives to the aqueous solution may or may not be soluble in the aqueous base. If the optional additives are not soluble in the aqueous solution, then they should be well dispersed in the aqueous solution.

The process comprises a step of a) introducing the aqueous solution into a chamber. The introduction of the aqueous solution into the chamber can be done via a variety of methods. For example, the solution can be placed in a vessel that is subsequently pressurized via the action of a piston or a pump or a screw or increased atmospheric pressure, for example, nitrogen or air, in order to force or extrude the solution through a nozzle or spinneret and into the chamber. In other embodiments, the aqueous solution can be introduced into the chamber via the action of gravity, for example, allowing the aqueous solution to flow through an opening in a suitable vessel through the spinneret into the chamber. The solution can be introduced into the chamber through a single orifice or multiple orifices, for example, 2 to 100 or even up to several thousand orifices.

The chamber further comprises an opening for a pressurized gas to be introduced into the chamber and an opening to allow the fibers to exit the chamber. The pressurized gas can be a gas that is not reactive with the water insoluble α-(1,3→glucan) polymer, for example, air, nitrogen, helium, argon, or a combination thereof. The pressurized gas is typically a dry gas, for example, a gas that has a water content of less than or equal to 10% or 5% or 1% by weight. Contacting the pressurized gas with the aqueous stream in the chamber forms the water insoluble α-(1,3→glucan) polymer into fibers. In other embodiments, contact of the pressurized gas with the water insoluble α-(1,3→glucan) polymer can help to evaporate at least a portion of the water from the aqueous solution, thereby beginning the formation of the fibers of the water insoluble α-(1,3→glucan) polymer in the chamber. In some embodiments, the pressurized gas can be introduced into the chamber at a velocity in the range of from 10 to 340 meters/second and is at a temperature of from 20° C. to 120° C. as it is introduced into the chamber. In other embodiments, the pressurized gas can be introduced into the chamber at a velocity in the range of from 30 to 250 meters/second or from 50 to 160 meters/second. The exit velocity can be a measured value or a calculated value. In some embodiments, the chamber can be electrified to provide an electroblown nonwoven web. In other embodiments, a nonwoven web can be formed wherein the chamber does not include an electrical charge.

The process may further comprise a step of fragmenting the aqueous solution with the pressurized gas prior to step (c), collecting the fibers to form the nonwoven web. In some embodiments, the aqueous solution introduced into the chamber can be a steady stream of the aqueous solution. When viewing the so-produced nonwoven web, for example, using a scanning electron micrograph, relatively few, if any, fiber ends are present. As the pressure of the pressurized gas increases, the steady stream of aqueous solution can be broken or fragmented, thereby forming relatively shorter fibers. The pressure at which the fragmentation occurs can vary depending upon several factors, including, for example, the concentration of the water insoluble α-(1,3→glucan) polymer in the aqueous solution, the viscosity of the aqueous solution, the amount and type of additives that can optionally be present in the aqueous solution or a combination thereof. One or ordinary skill in the art would be able to vary the process parameters in order to fragment the aqueous solution as desired.

The pressurized gas, any fibers that have formed and/or the aqueous solution upon leaving the chamber enter a zone of lower pressure. In some embodiments, the zone of lower pressure is at atmospheric pressure. In the zone of lower pressure, the aqueous solution forms fibers of the water insoluble α-(1,3→glucan) polymer. The fibers are then collected to form the nonwoven web of fibers in step c). The fibers can be collected on any suitable substrate. In some embodiments, the substrate can be a solid substrate, for example, a metal plate, metal roll, a polymeric plate, a polymeric roll, or a polymeric belt. In other embodiments, the substrate can be a perforated substrate, for example, a metal screen or a polymeric screen. Any of these substrates can be stationary or moving. The use of a screen or a perforated screen can allow the fibers to be collected on one side of the screen while an area of low pressure can be applied to the opposite side of the screen, allowing for more efficient collection of the fibers. The area of low pressure can also be used to remove at least a portion of the water from the aqueous solution.

The fibers that are collected on the substrate comprise at least a portion of the water from the aqueous solution. These wet fibers can, in some embodiments, have enough polymer mobility to intermix one fiber to another fiber in contact with it to have polymer entanglements, thereby forming a spunbond nonwoven web. In other embodiments, there is very little polymer chain entanglement within adjacent fibers, resulting in a relatively loose nonwoven web.

The process can optionally further comprise a step d) removing at least a portion of the water and/or aqueous base from the nonwoven web of fibers. The step of removing at least a portion of the water and/or base can be accomplished by evaporation, by washing the nonwoven web with a water miscible solvent, water, an acid, or by a combination thereof. For example, at least a portion of the water can be removed by utilizing a low pressure on one side of the screen used to collect the fibers. In other embodiments, at least a portion of the water and the base can be removed by washing the nonwoven web with a solvent, for example, methanol or ethanol, followed by washing the nonwoven web with water. Any remaining base, for example sodium hydroxide and/or potassium hydroxide, can be removed by washing the nonwoven web with water and/or an acid. The acid can be acid or an aqueous acid. Suitable examples can include, for example, glacial acetic acid, aqueous acetic acid, aqueous hydrochloric acid, aqueous sulfuric acid, aqueous citric acid, or a combination thereof. In still further embodiments, the acid is an aqueous mineral acid or an aqueous organic acid.

The nonwoven web can then be dried. The step of drying can be accomplished by increasing the temperature, lowering the pressure, blowing air onto the nonwoven web, or by a combination thereof.

Optionally, the nonwoven web can be finished using any method known in the art. Suitable finishing steps can include, for example, mechanical finishing and/or chemical finishing. Further examples of mechanical finishing can be calendering, brushing, mechanical bonding, embossing, heating, laminating, creeping, crushing, or a combination thereof. Suitable chemical finishing can include, for example, dyeing, chemical bonding, printing, surfacing, sizing, application of antimicrobial finishes, flame retardant finishes, or a combination thereof. The finishing steps can comprise a combination of both chemical and mechanical finishing in any workable order.

The thus formed nonwoven web can be used, for example, for personal hygiene wipes, filtration media, gowns, surgical suits, shoe covers, caps, wound dressings, geotextiles, carpet backing, one or more layers in a multilayer laminate, shopping bags, porous packaging, thermal and acoustic insulation, disposable clothing, diapers, training pants, swimwear, incontinence garments, pads, sanitary napkins, as well as antimicrobial surgical gowns and bandages, protective workwear garments such as coveralls and lab coats.

The disclosure comprises several embodiments; wherein the first embodiments comprises:

1. A process comprising:
   a) introducing an aqueous solution of a water insoluble α-(1,3→glucan) polymer into a chamber;
   b) contacting a pressurized gas with the aqueous solution of step (a) in the chamber to form fibers; and
   c) collecting the fibers to form a nonwoven web;
wherein the aqueous solution comprises the water insoluble α-(1,3→glucan) polymer in an aqueous base, and wherein the water insoluble α-(1,3→glucan) polymer has a ratio of apparent DPw to true DPw in the range of from 2 to 15.

2. The process of embodiment 1 further comprising a step of fragmenting the aqueous solution with the pressurized gas prior to step (c), collecting the fibers.

3. The process of any one of embodiments 1 or 2 further comprising a step of:
   d) removing at least a portion of the water and/or aqueous base from the nonwoven web of fibers.

4. The process of any one of embodiments 1, 2 or 3 wherein the nonwoven web of fibers is washed with water or acid.

5. The process of any one of embodiments 1, 2, 3 or 4 wherein the water insoluble α-(1,3→glucan) polymer is a linear polymer having greater than or equal to 99% of α-1,3-glycosidic linkages and less than 1% α-1,3,6-glycosidic branch points and a number average degree of polymerization in the range of from 55 to 10,000.

6. The process of any one of embodiments 1, 2, 3, 4 or 5 wherein the nonwoven web consists essentially of the water insoluble α-(1,3→glucan) polymer.

7. The process of any one of embodiments 1, 2, 3, 4, 5 or 6 wherein the water insoluble α-(1,3→glucan) polymer has a number average degree of polymerization in the range of from 55 to 10,000.

8. The process of any one of embodiments 1, 2, 3, 4, 5, 6 or 7 wherein pressurized gas is air.

9. The process of any one of embodiments 1, 2, 3, 4, 5, 6, 7 or 8 wherein the water insoluble α-(1,3→glucan) polymer is produced by a glucosyltransferase enzyme having 90% or greater sequence identity to Gtf J.

10. The process of any one of embodiments 1, 2, 3, 4, 5, 6, 7, 8 or 9 wherein the aqueous solution comprises in the range of from 5 to 30% by weight of the water insoluble α-(1,3→glucan) polymer, wherein the percentage by weight is based on the total amount of the aqueous solution.

11. The process of any one of embodiments 1, 2, 3, 4, 5, 6, 7, 8, 9, or 10 wherein the aqueous base comprises aqueous sodium hydroxide or aqueous potassium hydroxide.

12. A nonwoven web comprising water a insoluble α-(1,3→glucan) polymer, wherein the water insoluble α-(1,3→glucan) polymer comprises 90% or greater α-1,3-glycosidic linkages, less than 1% by weight of α-1,3,6-glycosidic branch points, a number average degree of polymerization in the range of from 55 to 10,000, and a ratio of apparent DPw to true DPw in the range of from 2 to 10.

13. The nonwoven web of embodiment 12 wherein the water insoluble α-(1,3→glucan) polymer has a number average degree of polymerization in the range of from 75 to 1,000.

14. The nonwoven web of any one of embodiments 12 or 13 wherein the water insoluble α-(1,3→glucan) polymer is produced by a glucosyltransferase enzyme having 90% or greater sequence identity to Gtf J.

15. The nonwoven web of any one of embodiments 12, 13, or 14 wherein the water insoluble α-(1,3→glucan) polymer is a linear polymer having greater than or equal to 99% of α-1,3-glycosidic linkages and less than 1% α-1,3,6-glycosidic branch points.

16. A nonwoven web of any one of embodiments 12, 13, 14, or 15, made by the process of any one of embodiments 1, 2, 3, 4, 5, 6, 7, 8, 9, 10, or 11.

EXAMPLES

Unless otherwise stated, all ingredients are available from Sigma-Aldrich, St. Louis, Mo.

Preparation of Water Insoluble α-(1,3→Glucan) Polymer

The water insoluble α-(1,3→glucan) polymer was produced according to a method of U.S. Pat. No. 8,871,474. The water insoluble α-(1,3→glucan) polymer had a number average degree of polymerization of about 300 and >98% α-1,3 glycosidic linkages. The apparent DPw was 2150 and the true DPw was 860, to give an apparent DPw/true DPw ratio of 2.5

Preparation of Nonwoven Web #1

A solution of the water insoluble α-(1,3→glucan) polymer was produced by adding 36 grams of the polymer portionwise to a solution of 18 grams of sodium hydroxide in 346 grams of water under agitation. After the addition was complete, the mixture was agitated for an additional 5 minutes and the solution was allowed to sit for one hour in order to de-gas.

25 Milliliters of the solution was added to a spin reservoir leading to a 400 micrometer capillary. The reservoir was pressurized to about 3.5 kilograms/centimeter$^2$ and heated to 33° C. Air at 0.28 kg/cm$^2$ was blown into the spin chamber. The solution was spun onto a moving drum having a width of about 30.5 centimeters and a diameter of about 20.3 centimeters, without the application of vacuum onto the roll. The distance between the spin chamber and the drum roll was 45 centimeters. The result was a loose web of fibers.

Preparation of Nonwoven Web #2

A solution of the water insoluble α-(1,3→glucan) polymer was produced by adding 36 grams of the polymer portionwise to a solution of 18 grams of sodium hydroxide in 346 grams of water under agitation. After the addition was complete, the mixture was agitated for an additional 5 minutes and the solution was allowed to sit for one hour in order to de-gas.

25 Milliliters of the solution was added to a spin reservoir leading to a 400 micrometer capillary. The reservoir was pressurized to about 3.5 kilograms/centimeter$^2$ and heated to 33° C. Air at 0.28 kg/cm$^2$ was blown into the spin chamber. The solution was spun onto a vacuum panel. The distance between the spin chamber and the vacuum panel was 65 centimeters. The nonwoven web was removed to give 12.1 grams of a crude nonwoven web. The web was allowed to soak in methanol for 20 minutes. The web was removed from the methanol, the methanol was discarded and the web was soaked a second time in methanol for 20 minutes. The web was removed and was soaked in deionized water for 20 minutes. After removing the web from the deionized water bath, it was allowed to dry in air over the weekend. The result was a nonwoven web having a weight of 7.1 grams.

What is claimed is:

1. A process comprising:
   (a) introducing an aqueous solution of a water insoluble α-(1,3→glucan) polymer to a chamber;
   (b) contacting a pressurized gas with the aqueous solution of step (a) in the chamber to form fibers; and
   (c) collecting the fibers to form a nonwoven web;
   wherein the aqueous solution comprises the water insoluble α-(1,3→glucan) polymer in an aqueous base, and wherein the water insoluble α-(1,3→glucan) polymer has 90% or greater α-1,3-glycosidic linkages.

2. The process of claim 1, further comprising a step of fragmenting the aqueous solution with the pressurized gas prior to step (c).

3. The process of claim 1, further comprising a step of:
   (d) removing at least a portion of water and/or the aqueous base from the nonwoven web.

4. The process of claim 1, wherein the nonwoven web is washed with water or acid.

5. The process of claim 1, wherein the water insoluble α-(1,3→glucan) polymer has greater than or equal to 99% α-1,3-glycosidic linkages.

6. The process of claim 1, wherein the nonwoven web consists essentially of the water insoluble α-(1,3→glucan) polymer.

7. The process of claim 1, wherein the water insoluble α-(1,3→glucan) polymer has a number average degree of polymerization in the range of 75 to 1000.

8. The process of claim 1, wherein the pressurized gas is air.

9. The process of claim 1, wherein the aqueous solution comprises 5 to 30% by weight of the water insoluble α-(1,3→glucan) polymer, wherein the percentage by weight is based on the total amount of the aqueous solution.

10. The process of claim 1, wherein the aqueous base comprises aqueous sodium hydroxide or aqueous potassium hydroxide.

11. The process of claim 1, wherein the chamber has an electrical charge.

12. The process of claim 1, wherein step (b) comprises increasing the pressure of the pressurized gas thereby forming shorter fibers prior to step (c).

13. The process of claim 1, wherein the water insoluble α-(1,3→glucan) polymer has less than 1% α-1,3,6-glycosidic branch points.

14. The process of claim 1, wherein the water insoluble α-(1,3→glucan) polymer has a number average degree of polymerization of 55 to 10000.

15. The process of claim 1, wherein the aqueous solution in step (a) is introduced to the chamber from a vessel, wherein the aqueous solution flows through at least one orifice of the vessel into the chamber.

16. The process of claim 15, wherein the aqueous solution is forced through said at least one orifice of the vessel by pressure.

17. The process of claim 15, wherein the aqueous solution flows through said at least one orifice of the vessel by gravity.

18. The process of claim 1, wherein the aqueous solution in step (a) is introduced to the chamber from a nozzle or spinneret.

19. The process of claim 18, wherein the aqueous solution is forced through the nozzle or spinneret by pressure.

20. The process of claim 18, wherein the aqueous solution flows through the nozzle or spinneret by gravity.

21. The process of claim 1, wherein the pressurized gas is introduced to the chamber at a velocity of 10 to 340 meters/second.

22. The process of claim 1, wherein the pressurized gas is introduced to the chamber at a velocity of 30 to 250 meters/second.

23. The process of claim 1, wherein the pressurized gas is introduced to the chamber at a velocity of 50 to 160 meters/second.

24. The process of claim 1, wherein the fibers are collected onto a metal plate, metal roll, polymeric plate, polymeric roll, or polymeric belt.

25. The process of claim 1, wherein the fibers are collected onto a perforated substrate.

26. The process of claim 1, wherein the fibers are collected onto a metal screen or polymeric screen.

27. The process of claim 1, wherein the fibers are collected onto a solid substrate that is stationary or moving.

* * * * *